(12) United States Patent
Knox et al.

(10) Patent No.: US 9,622,912 B2
(45) Date of Patent: *Apr. 18, 2017

(54) METHOD FOR MODIFYING THE REFRACTIVE INDEX OF AN OPTICAL MATERIAL

(71) Applicant: University of Rochester, Rochester, NY (US)

(72) Inventors: Wayne H. Knox, Pittsford, NY (US); Li Ding, San Jose, CA (US); Jay F. Kunzler, Canandaigua, NY (US); Dharmendra Jani, Keller, TX (US)

(73) Assignee: University of Rochester, Rochester, NY (US)

( * ) Notice: Subject to any disclaimer, the term of this patent is extended or adjusted under 35 U.S.C. 154(b) by 212 days.

This patent is subject to a terminal disclaimer.

(21) Appl. No.: 14/564,207

(22) Filed: Dec. 9, 2014

(65) Prior Publication Data

US 2015/0126979 A1    May 7, 2015

Related U.S. Application Data

(60) Division of application No. 13/686,952, filed on Nov. 28, 2012, now Pat. No. 8,932,352, which is a continuation of application No. 12/846,950, filed on Jul. 30, 2010, now Pat. No. 8,337,553, which is a division of application No. 11/948,298, filed on Nov.

(Continued)

(51) Int. Cl.
| | |
|---|---|
| *A61F 2/16* | (2006.01) |
| *A61F 9/008* | (2006.01) |
| *G02C 7/02* | (2006.01) |
| *B29D 11/00* | (2006.01) |
| *B29D 11/02* | (2006.01) |
| *C08J 7/12* | (2006.01) |
| *A61B 18/20* | (2006.01) |
| *A61F 2/14* | (2006.01) |

(Continued)

(52) U.S. Cl.
CPC ............ *A61F 9/008* (2013.01); *A61B 18/20* (2013.01); *A61F 2/14* (2013.01); *A61F 2/16* (2013.01); *A61L 27/16* (2013.01); *A61L 27/52* (2013.01); *B29D 11/00355* (2013.01); *B29D 11/00461* (2013.01); *B29D 11/023* (2013.01); *C08J 7/12* (2013.01); *C08J 7/123* (2013.01); *G02C 7/022* (2013.01); *G02C 2202/12* (2013.01); *G02C 2202/14* (2013.01)

(58) Field of Classification Search
CPC ..... G02B 1/043; A61L 27/16; A61L 2430/16; A61F 2/16; A61F 9/00804; A61F 9/00827; C08L 83/04; B29D 11/00; B29D 11/00355
USPC ............................................. 219/383, 121.71
See application file for complete search history.

(56) References Cited

U.S. PATENT DOCUMENTS

| | | | | |
|---|---|---|---|---|
| 2008/0001320 A1* | 1/2008 | Knox | ...................... | A61F 9/008 264/1.37 |
| 2009/0287306 A1* | 11/2009 | Smith | ................... | A61F 2/1627 623/5.16 |

\* cited by examiner

*Primary Examiner* — David H Willse
*Assistant Examiner* — Tiffany Shipmon
(74) *Attorney, Agent, or Firm* — Thomas B. Ryan, Patent Agent; Harter Secrest & Emery LLP

(57) ABSTRACT

An optical device comprising an optical hydrogel with select regions that have been irradiated with laser light having a pulse energy from 0.01 nJ to 50 nJ and a wavelength from 600 nm to 900 nm. The irradiated regions are characterized by a positive change in refractive index of from 0.01 to 0.06, and exhibit little or no scattering loss. The optical hydrogel is prepared with a hydrophilic monomer.

20 Claims, 10 Drawing Sheets

Related U.S. Application Data

30, 2007, now Pat. No. 7,789,910, which is a continuation-in-part of application No. 11/745,746, filed on May 8, 2007.

(60) Provisional application No. 60/817,027, filed on Jun. 28, 2006.

(51) Int. Cl.
*A61L 27/16* (2006.01)
*A61L 27/52* (2006.01)

METHOD FOR MODIFYING THE REFRACTIVE INDEX OF AN OPTICAL MATERIAL

This patent application is a Division of U.S. patent application Ser. No. 13/686,952 filed Nov. 28, 2012, which is a Continuation of U.S. patent application Ser. No. 12/846,950 filed Jul. 30, 2010, now U.S. Pat. No. 8,337,553, which is a Division of U.S. patent application Ser. No. 11/948,298 filed Nov. 30, 2007, now U.S. Pat. No. 7,789,910, which is a Continuation-in-part of U.S. patent application Ser. No. 11/745,746 filed May 8, 2007, which claims the benefit of U.S. Provisional Application No. 60/817,027 filed Jun. 28, 2006.

The present invention relates to a method of using a laser to modify the refractive index of an optical device, and the resulting optical device.

BACKGROUND OF THE INVENTION

In general, there are two types of intraocular lenses. One type replaces the eye's natural lens, usually to replace a cataractous lens. The other type is used to supplement an existing lens and functions as a permanent corrective lens. This type of lens (referred to as a phakic IOL) is implanted in the anterior or posterior chamber to correct refractive errors of the eye. In theory, the power for either type of IOL required for enmetropia (i.e., point focus on the retina from light originating at infinity) can be precisely calculated. The power of the implanted lens is selected based on pre-operative measurements of ocular length and corneal curvature to enable the patient to see without or with little vision correction. Unfortunately, due to errors in measurement, variable lens positioning or wound healing, most patients undergoing cataract surgery will not enjoy optimal vision without some form of vision correction following the surgery (Brandser et al., Acta Opthalmol Scand 75:162 165 (1997); Oshika et al., J Cataract Refract Surg 24:509 514 (1998). Because the power of present IOLs cannot be adjusted post-implantation, the patient typically must use additional corrective lenses such as eye glasses or contact lenses.

One potential solution to the foregoing problem is a light-adjustable intraocular lens whose refraction properties can be modified following insertion of the lens into a human eye. Such a lens is reported in U.S. Pat. No. 6,450,642, hereafter referred to as the Calhoun Patent. The light-adjustable lens is said to comprise (i) a first polymer matrix and (ii) a refraction modulating composition (RMC) that is capable of stimulus-induced polymerization. As stated, when a portion of the described lens is exposed to light of sufficient intensity, the RMC forms a second polymer matrix. The process is said to result in a light adjusted, power-modified lens.

As described in the Calhoun Patent, the first polymer matrix and the RMC are selected such that the components that comprise the RMC are capable of diffusion within the first polymer matrix. Put another way, a loose first polymer matrix will tend to be paired with larger RMC components and a tight first polymer matrix will tend to be paired with smaller RMC components. Upon exposure to an appropriate energy source (e.g., heat or light), the RMC typically forms a second polymer matrix in the exposed region of the optical element. After exposure, the RMC in the unexposed region will migrate into the exposed region over time. The amount of RMC migration into the exposed region is time dependent and may be precisely controlled. If enough time is permitted, the RMC components will re-equilibrate and redistribute throughout the lens material (i.e., the first polymer matrix, including the exposed region). When the region is re-exposed to the energy source, the RMC that has since migrated into the region polymerizes to further increase the formation of the second polymer matrix. This process (exposure followed by an appropriate time interval to allow for diffusion) may be repeated until the exposed region of the optical element has reached the desired property (e.g., power, refractive index, or shape). The entire optical element is then exposed to an energy source to "lock-in" the desired lens property by polymerizing the remaining RMC in the lens material. Overall, the power of the lens is changed by a shape change caused by the migrating of the RMC and subsequent polymerization(s).

U.S. Pat. No. 7,105,110 describes a method and instrument to irradiate a light adjustable lens with an appropriate amount of radiation in an appropriate pattern. The method is said to include aligning a source of the modifying radiation so as to impinge the radiation onto the lens in a pattern, and controlling the quantity of the impinging radiation. The quantity of the impinging radiation is controlled by controlling the intensity and duration of the irradiation.

There exists an ongoing need for new materials and processes to improve a patient's vision following cataract surgery. In particular, there is a need for an IOL material whose refractive power can be modified by a change in the refractive index of the lens material post-operative implantation.

SUMMARY OF THE INVENTION

An optical device comprising an optical hydrogel with select regions that have been irradiated with laser light having a pulse energy from 0.01 nJ to 50 nJ and a wavelength from 600 nm to 900 nm. The irradiated regions are characterized by a positive change in refractive index of from 0.01 to 0.06, and exhibit little or no scattering loss. The optical hydrogel is prepared with a hydrophilic monomer.

A method of changing the index of refraction of an optical hydrogel that is a component of an optical device implanted in the eye of a patient for vision correction. The method comprises providing a physician with a laser system to irradiate select regions of the optical hydrogel following implantation of the optical device into the eye of the patient. The laser system comprises a laser having a pulse energy from 0.01 nJ to 50 nJ and a light wavelength from 600 nm to 900 nm. The irradiated regions are formed by scanning the laser light in an X-Y plane perpendicular to the laser beam, and the irradiated regions characterized by a positive change in refractive index of from 0.01 to 0.06 and exhibit little or no scattering loss.

BRIEF DESCRIPTION OF THE DRAWINGS

The invention will be better understood from the following description and in consideration with the accompanying figures. It is to be expressly understood, however, that each of the figures is provided to further illustrate and describe the invention and is not intended to further limit the invention claimed.

DETAILED DESCRIPTION OF THE INVENTION

Figure 1:
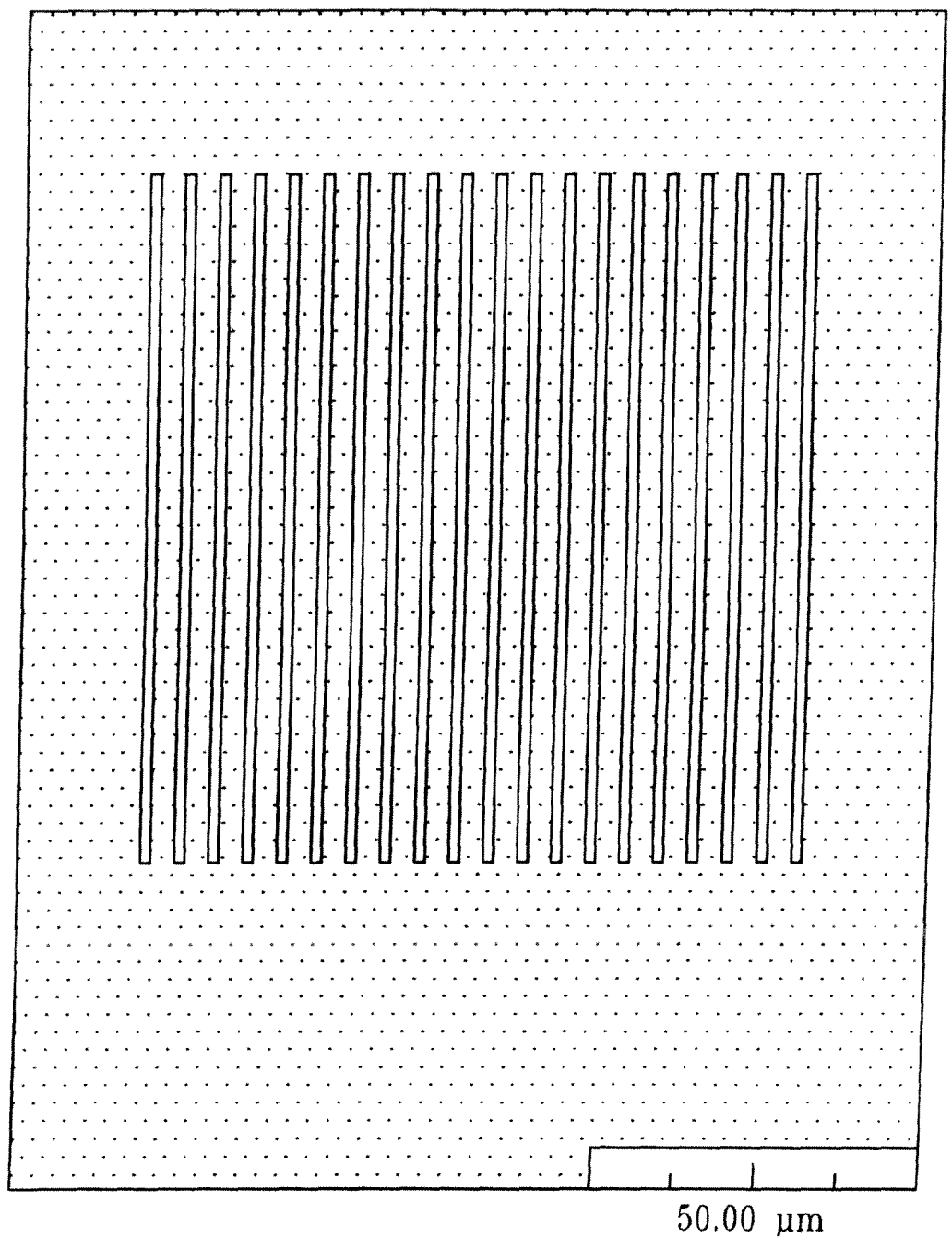
FIG. 1 is a microscope photograph of a line grating written in an optical, polymeric material produced by laser irradiation.

If very short laser pulses of sufficient energy are tightly focused on an optical, polymeric material, the high intensity of light at the focus point causes a nonlinear absorption of photons (typically multi-photon absorption) and leads to a change in the refractive index of the material at the focus point. Moreover, the region of the material just outside the focal region is minimally affected by the laser light. Accordingly, select regions of an optical, polymeric material can be modified with a laser resulting in a change in the refractive index in these regions.

The invention is directed to a method for modifying the refractive index of an optical device. The method comprises irradiating select regions of an optical, polymeric material of the device with a focused, visible or near-IR laser having a pulse energy from 0.05 nJ to 1000 nJ. The irradiated regions exhibit no significant differences in the Raman spectrum with respect to the non-irradiated optical, polymeric material. Also, the irradiated regions exhibit little or no scattering loss, which means that the structures formed in the irradiated regions are not clearly visible under appropriate magnification without contrast enhancement.

The pulse energy of the focused laser used in the method will in-part depend on the type of optical material that is being irradiated, how much of a change in refractive index is desired and the type of structures one wants to imprint within the material. The selected pulse energy will also depend upon the scan rate at which the structures are written into the optical material. Typically, greater pulse energies will be needed for greater scan rates. For example, some materials will call for a pulse energy from 0.2 nJ to 100 nJ, whereas other optical materials will call for a pulse energy from 0.5 nJ to 10 nJ.

The pulse width must be preserved so that the pulse peak power is strong enough to exceed the nonlinear absorption threshold of the optical material. However, the glass of the focusing objective(s) significantly increases the pulse width due to the positive dispersion of the glass. A compensation scheme is used to provide a corresponding negative dispersion that can compensate for the positive dispersion introduced by the focusing objective(s). Accordingly, the term "focused" in this application refers to the focusing of light from a laser within an optical, polymeric material using a compensation scheme to correct for the positive dispersion introduced by the focusing objective(s). The compensation scheme can include an optical arrangement selected from the group consisting of at least two prisms and at least one mirror, at least two diffraction gratings, a chirped mirror and dispersion compensating mirrors to compensate for the positive dispersion introduced by the focus objective.

In one embodiment, the compensation scheme comprises at least one prism, in many cases at least two prisms, and at least one mirror to compensate for the positive dispersion of the focusing objective. In another embodiment, the compensation scheme comprises at least two gratings to compensate for the positive dispersion of the focusing objective. Any combination of prisms, gratings and/or mirrors can be used for the compensation scheme.

The use of the compensation scheme with the focusing objective can generate pulses with a pulse energy from 0.01 nJ to 100 nJ, or from 0.01 nJ to 50 nJ, and a pulse width of from 4 fs to 200 fs. At times, it can be advantageous to generate a laser pulse with energies from 0.2 nJ to 20 nJ, and a pulse width of from 4 fs to 100 fs. Alternatively, it can be advantageous to generate a laser pulse with energies from 0.2 nJ to 10 nJ and a pulse width of from 5 fs to 50 fs.

The laser will generate light with a wavelength in the range from violet to near-infrared radiation. In various embodiments, the wavelength of the laser is in the range from 400 nm to 1500 nm, from 400 nm to 1200 nm or from 600 nm to 900 nm.

In one particular embodiment, the laser is a pumped Ti:sapphire laser with an average power of 10 mW to 1000 mW. Such a laser system will generate light with a wavelength of approximately 800 nm. In another embodiment, an amplified fiber laser that can generate light with a wavelength from 1000 nm to 1600 nm can be used The laser will have a peak intensity at focus of greater than $10^{13}$ W/cm$^2$. At times, it may be advantageous to provide a laser with a peak intensity at focus of greater than $10^{14}$ W/cm$^2$, or greater than $10^1$ W/cm$^2$.

The method of the invention provides an opportunity for an ocular surgeon to modify the refractive index of an optical device, e.g., an intraocular lens or corneal inlay, after the device has been implanted into the eye of a patient. The method allows the surgeon to correct any aberrations as a result of the surgery. The method also allows the surgeon to adjust the power of the lens or inlay by increasing the refractive index in the irradiated regions. For example, starting from a lens of selected power (will vary according to the ocular requirements of the patient), the surgeon can further adjust the refractive properties of the lens to correct a patients vision based upon the individual needs of the patient. In essence, an intraocular lens would essentially function like contact lenses or glasses to individually correct for the refractive error of a patient's eye. Moreover, because the implanted lens can be adjusted by increasing the refractive index of select regions of the lens, post-operative refractive errors resulting from pre-operative measurement errors, variable lens positioning during implantation and wound healing (aberrations) can be corrected or fine tuned in-situ.

For instance, cataract surgery typically requires that the natural lens of each eye be replaced with an intraocular lens (IOL). Following insertion of the IOL the surgeon can correct for aberrations resulting from the surgery or correct for slight misplacement of the IOL. Following surgery, and after allowing time for the wound to heal, the patient would return to the surgeon to have select regions of the IOL irradiated. These irradiated regions would experience a positive change in refractive index, which would correct for the aberrations as well as the patients needs for vision correction. In some instances, the surgeon would be able to adjust the IOL in one eye for distance and adjust the IOL in the opposite eye for reading.

Typically, the irradiated portions of the optical material will exhibit a positive change in refractive index of about 0.01 or more. In one embodiment, the refractive index of the region will increase by about 0.03 or more. In fact, applicants have measured a positive change in refractive index in an optical silicone-containing hydrogel of about 0.06.

It is to be understood by one of ordinary skill in the art, that the method of the invention modifies the optical properties of the material not by casting an optical material with nonreacted monomer (refraction modulation composition) followed by laser irradiation to promote additional polymerization chemistry as described in the Calhoun Patent, but rather by changing the refractive index of an already completely polymerized optical material. The term "completely polymerized" when used to characterize the optical materials used in the method means that the optical materials are 95% or more polymerized. One way to measure the completeness of a polymerized optical material is by near infra-red spectroscopy, which is used to qualitatively determine the vinyl content of the material. Simple gravimetric weight analysis can also be used.

The irradiated regions of the optical device formed by the method of the invention can be defined by two- or three-dimensional structures. The two- or three-dimensional structures can comprise an array of discrete cylinders. Alternatively, the two- or three-dimensional structures can comprise a series of lines (a grating) or a combination of an array of cylinders and a series of lines. Moreover, the two- or three-dimensional structures can comprise area or volume filled structures, respectively. These area or volume filled structures are formed by continuously scanning the laser over a select region of the polymeric material.

Nanometer-sized structures can also be formed by the zone-plate-array lithography method describe by R. Menon et al., Proc. SPIE, Vol. 5751, 330-339 (May 2005); Materials Today, p. 26 (February 2005).

In one embodiment, the irradiated regions of the optical device are defined by a series of lines in a two dimensional plane having a width from 0.2 µm to 3 µm, preferably a width from 0.6 µm to 1.5 µm and a height from 0.4 µm to 8 µm, preferably a height from 1.0 µm to 4 µm (height is measured in the z direction of the material, which is parallel to direction of the laser light). For example, one can generate a line grating comprising a plurality of lines with each line of any desired length, about 0.8 µm to about 1.5 µm in width and about 2 µm to 5 µm in height. The lines can be separated by as little as 1.0 µm (0.5 µm spacing), and any number of lines can be incorporated into the material. Moreover, the grating can be positioned at any selected depth (z-direction), and any number of line gratings can be generated at various depths into the material.

FIG. 1 is a microscope photograph with contrasting background of a line grating comprising 20 lines written into an optical material. Each line is about 100 µm in length, about 1 µm in width with a line separation of about 5 µm. The lines have a height of about 3 µm and were written into the material at a distance of about 100 µm from the top surface of the material. Similar microscope photographs exhibiting line gratings were obtained at a distance of about 200 µm and 400 µm from the top surface of the material, thereby demonstrating that structures can be written into the optical material at any selected depth.

Figure 2:
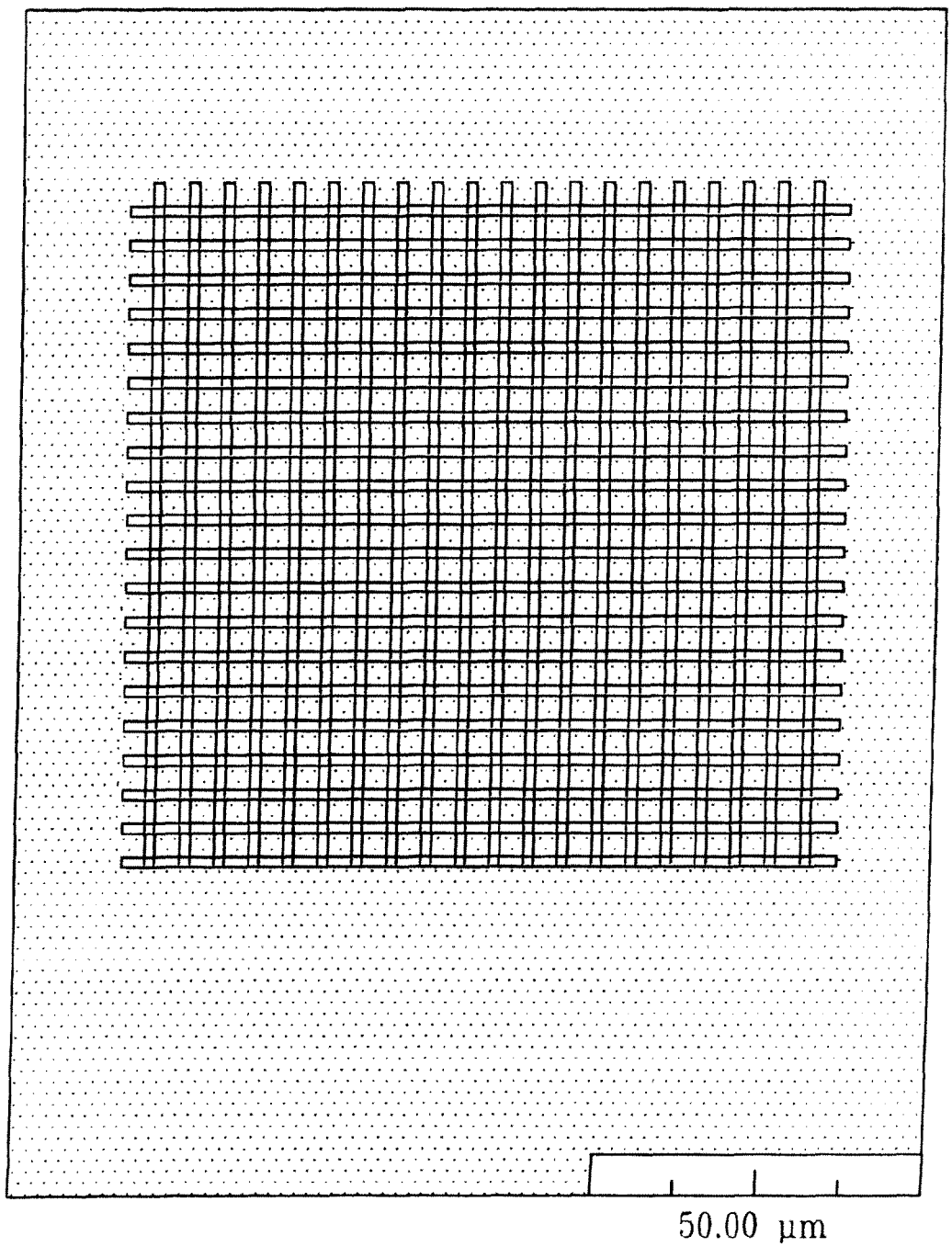
FIG. 2 is a microscope photograph of a line grating written above and orthogonal to another line grating in an optical, polymeric material produced by laser irradiation.

FIG. 2 is a microscopic photograph with contrasting background of one line grating written above and orthogonal to another line grating. Each of the gratings has a similar dimensional structure to that described for FIG. 1 above. One line grating is positioned about 100 µm into the material, and the other line grating is positioned about 110 µm into the material for a center-line, grating separation of about 10 µm. Again, each of these line structures has a height (depth) of about 3 µm.

Figure 3:
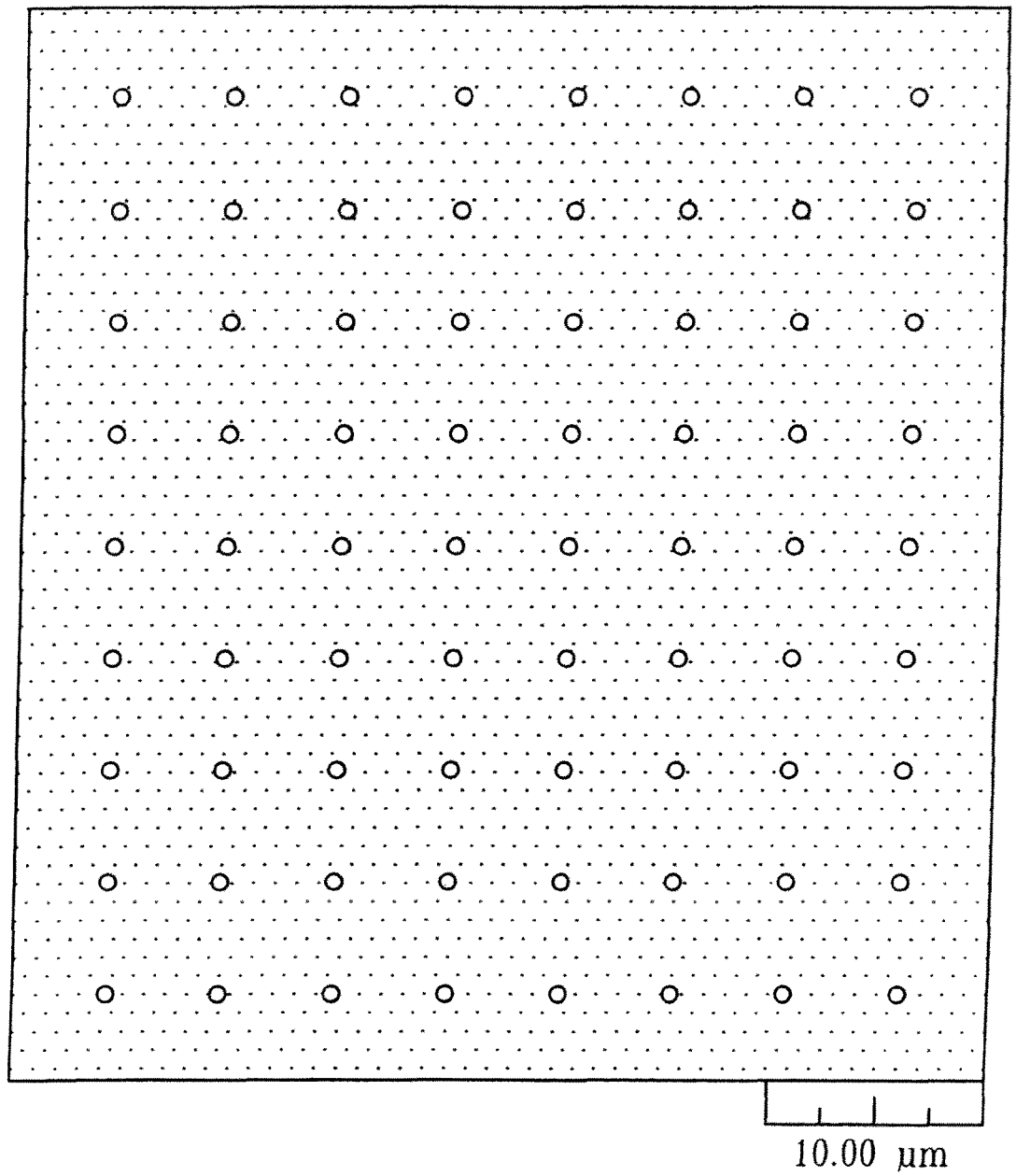
FIG. 3 is a microscope photograph of an array of cylinders etched in an optical, polymeric material produced by laser irradiation.

FIG. 3 is a microscopic photograph with contrasting background of an array of cylinders written into an optical material. Each cylinder is about 1 µm in diameter with a height of about 3 µm. The cylinders are separated by about 5 µm. The cylinders were etched into the material at a distance of about 100 µm from the top surface of the material.

Figure 4:
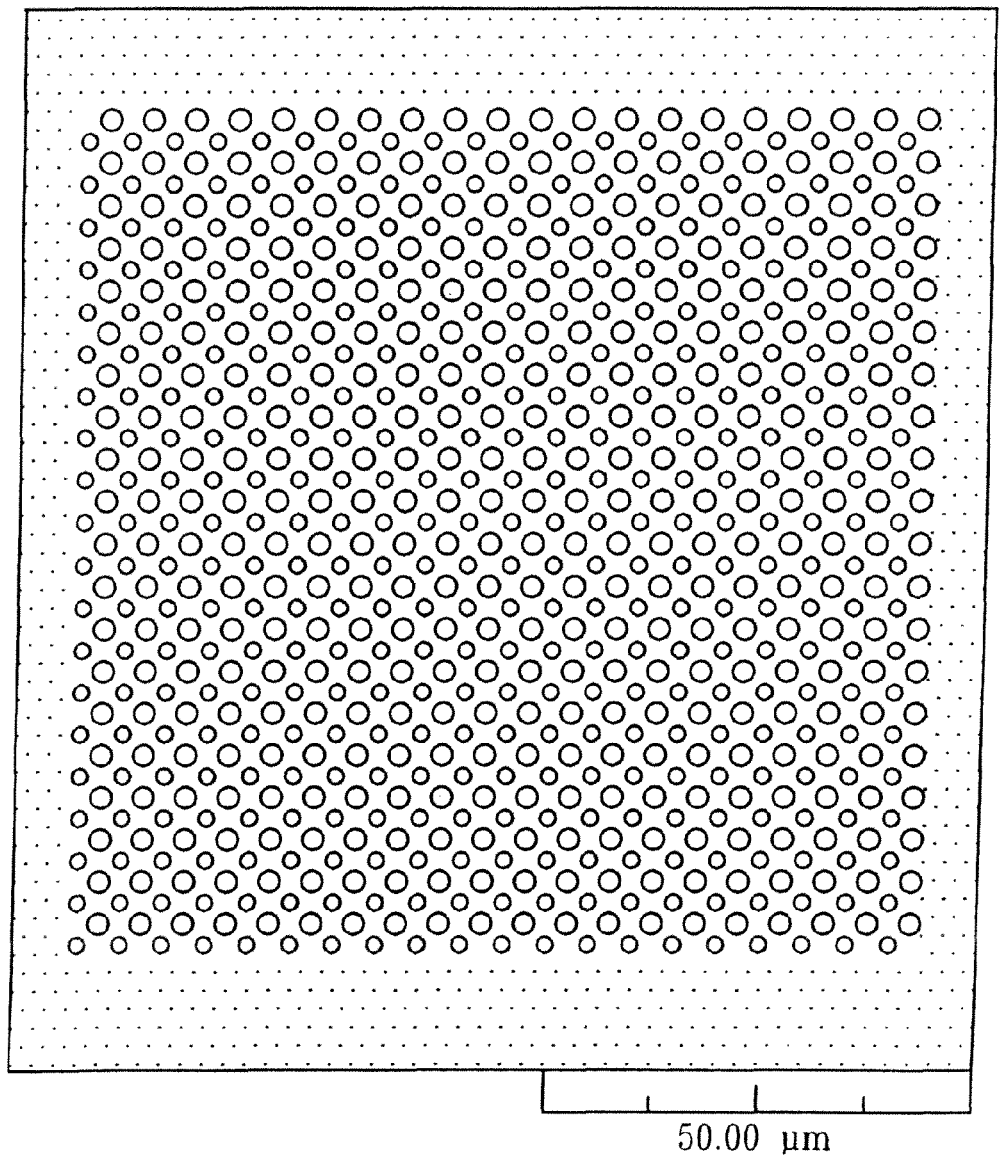
FIG. 4 is a microscope photograph of one array of cylinders (20×20) etched above and slightly offset to another array of cylinders (20×20) in an optical, polymeric material produced by laser irradiation.

FIG. 4 is a microscopic photograph with contrasting background of one array of cylinders (20×20) written above and slightly offset to another array of cylinders (20×20). Each of the cylinders has a similar dimensional structure to that described for FIG. 3 above. One array is positioned about 100 µm into the material, and the other array is positioned about 105 µm into the material for a center-line separation of about 5 µm. Each of the cylinders has a height (depth) of about 3 µm.

Figure 5:
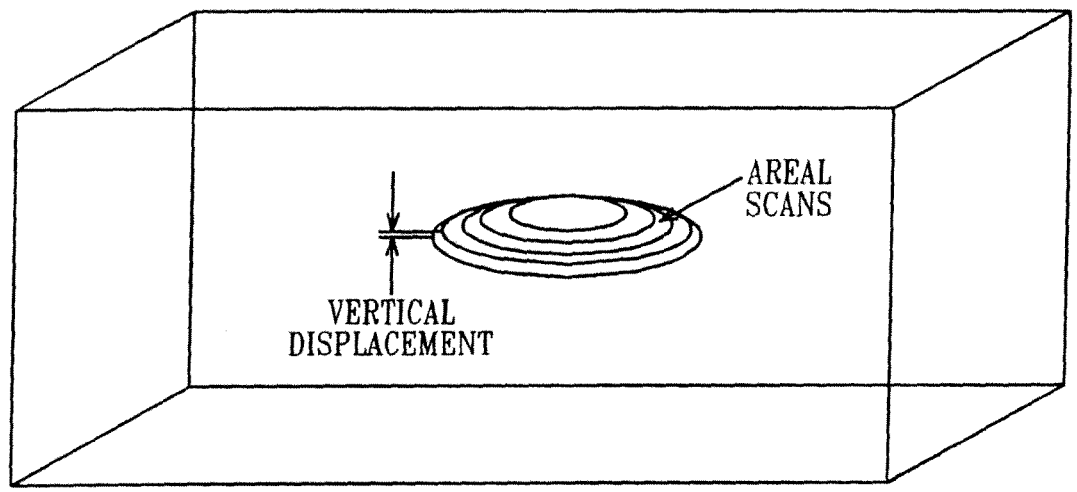
FIG. 5 is a schematic representation of a three-dimensional structure in an optical, polymeric material that can be produced by laser irradiation.
Figure 6:
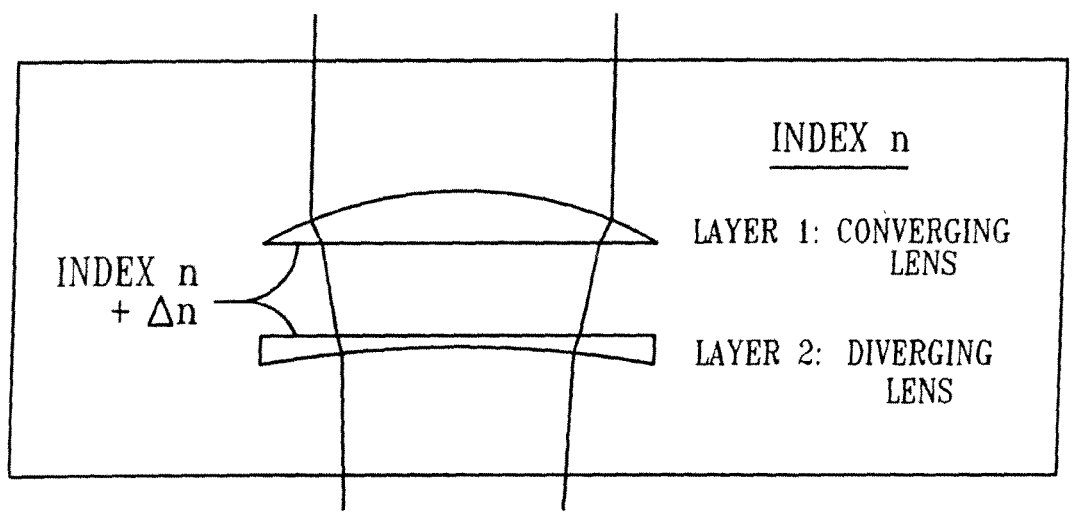
FIG. 6 is a schematic representation of creating a convex, plano or concave structure in an optical, polymeric material to yield a positive or negative correction.

The area-filled or volume-filled two- or three-dimensional structures can be formed by continuously scanning the laser over selected regions of the optical, polymeric material. Refractive-type optical devices can be micro-machined inside the volume of an optical, polymer material by repeatedly scanning a tightly focused beam of femtosecond pulses in an area segment. The area of the segment can be changed correspondingly with the depth of the scan, so as to produce three-dimensionally shaped lenses with spheric, aspheric, toroidal or cylindrical shapes as shown in FIG. 5. Although the refractive index change is positive (+0.02 to +0.06), these refractive corrective lenses can be made in various combinations of convex, plano- or concave to yield a positive correction, or negative correction, as shown in FIG. 6. The devices can be stacked vertically, written separately in different planes, so as to act as a single lens. Additional corrective layers can be written as desired.

1. A Laser and Optical Configuration for Modifying an Optical Material.

Figure 7:
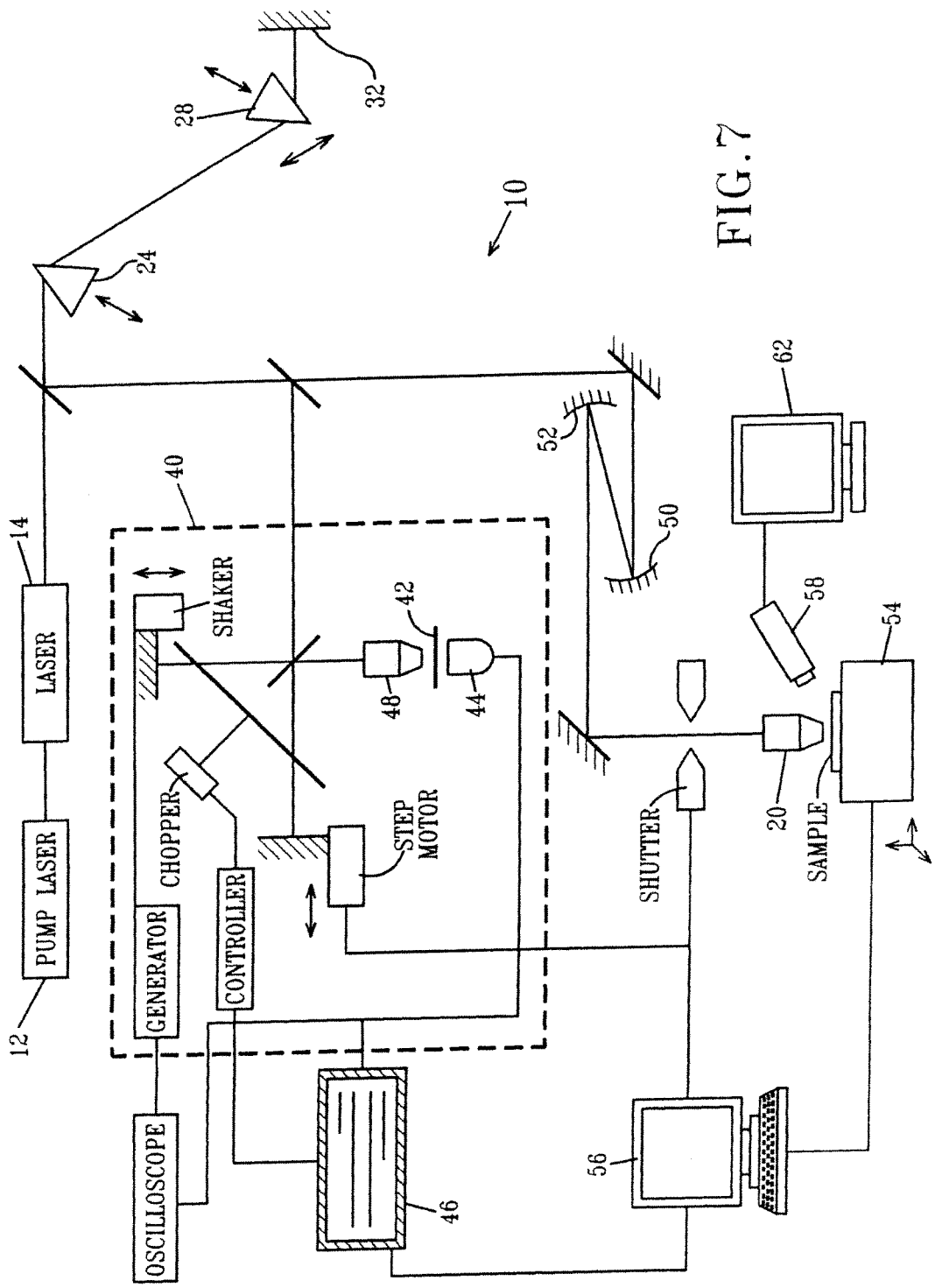
FIG. 7 is a schematic representation of the laser and optical system used to write the structures shown in FIGS. 1 to 4.
Figure 8:
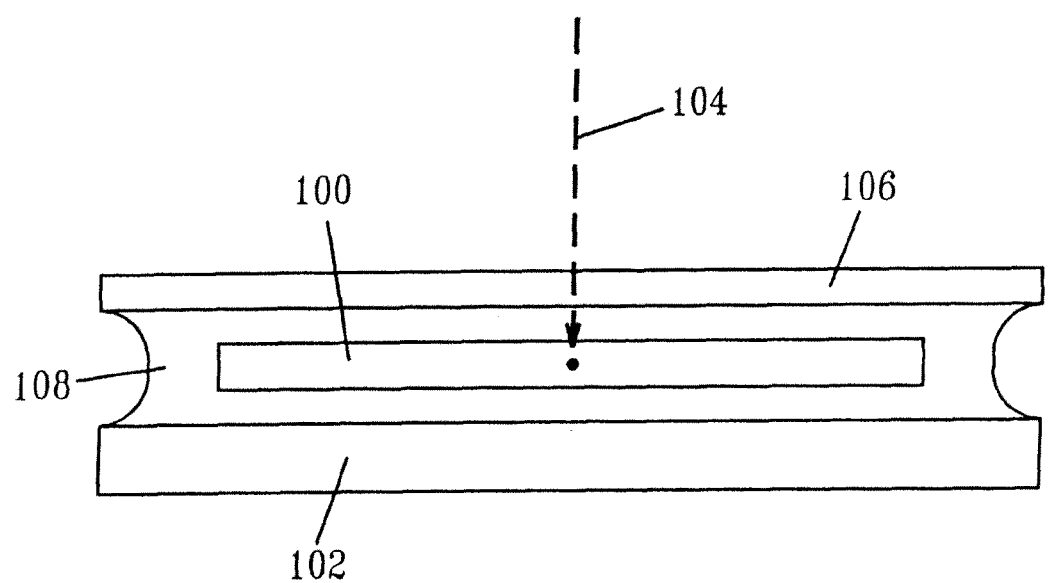
FIG. 8 shows schematically an arrangement of a sample for modification by a laser.

A non-limiting embodiment of a laser system 10 for irradiating an optical, polymeric material with a laser to modify the refractive index of the material in select regions is illustrated in FIG. 7. A laser source comprises a Kerr-lens mode-locked Ti:Sapphire laser 12 (Kapteyn-Murnane Labs, Boulder, Colo.) pumped by 4 W of a frequency-doubled Nd:YVO$_4$ laser 14. The laser generates pulses of 300 mW average power, 30 fs pulse width and 93 MHz repetition rate at wavelength of 800 nm. Because there is a reflective power loss from the mirrors and prisms in the optical path, and in particular, from the power loss of the objective 20, the measured average laser power at the objective focus on the material is about 120 mW, which indicates the pulse energy for the femtosecond laser is about 1.3 nJ.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity, compensation scheme is used to provide the negative dispersion that compensates for the positive dispersion introduced by the focusing objective. Two SF10 prisms 24 and 28 and one ending mirror 32 form a two-pass one-prism-pair configuration. We used a 37.5 cm separation distance between the prisms to compensate the dispersion of the microscope objective and other optics within the optical path.

A collinear autocorrelator 40 using third-order harmonic generation is used to measure the pulse width at the objective focus. Both $2^{nd}$ and $3^{rd}$ harmonic generation have been used in autocorrelation measurements for low NA or high NA objectives. We selected third order surface harmonic generation (THG) autocorrelation to characterize the pulse width at the focus of the high-numerical-aperture objectives because of its simplicity, high signal to noise ratio and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, we selected a transform-limited 27-fs duration pulse, which is focused by a 60×0.70NA Olympus LUCPlanFLN long-working-distance objective 48.

Because the laser beam will spatially diverge after it comes out of the laser cavity, a concave mirror pair 50 and 52 is added into the optical path in order to adjust the dimension of the laser beam so that the laser beam can optimally fills the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micro-machine different patterns in the materials with different scanning speed at different position and depth and different laser exposure time. In addition, a CCD camera 58 along with a monitor 62 is used beside the objective 20 to monitor the process in real time.

The method and optical apparatus described above can be used to modify the refractive index of an intraocular lens following the surgical implantation of the intraocular lens in a human eye.

Accordingly, the invention is directed to a method comprising identifying and measuring the aberrations resulting from the surgical procedure. Once the aberrations are identified and quantified using methods well known in the art of ophthalmology, this information is processed by a computer. Of course, information related to the requisite vision correction for each patient can also be identified and determined, and this information can also be processed by a computer. There are a number of commercially available diagnostic systems that are used to measure the aberrations. For example, common wavefront sensors used today are based on the Schemer disk, the Shack Hartmann wavefront sensor, the Hartmann screen, and the Fizeau and Twymann-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the optical structures to be written into the lens material to correct for those aberrations. These computer programs are well known to those of ordinary skill in the art. The computer than communicates with the laser-optical system and select regions of the lens are irradiated with a focused, visible or near-IR laser having a pulse energy from 0.05 nJ to 1000 nJ.

2. The Optical, Polymeric Materials

The optical, polymeric materials that can be irradiated by a visible or near-IR laser according to the methods described in this application can be any optical, polymeric material known to those of ordinary skill in the polymeric lens art, particularly those in the art familiar with optical materials used to make intraocular lenses. The optical, polymeric materials are of sufficient optical clarity, and will have a relatively high refractive index of approximately 1.40 or greater. Many of these materials are also characterized by a relatively high elongation of approximately 80 percent or greater.

A method of the present invention can be applied to a wide variety of optical materials. Non-limiting examples of such materials include those used in the manufacture of ophthalmic devices, such as contact lenses and IOLs. For example, the method of the present invention can be applied to siloxy-containing polymers, acrylic polymers, other hydrophilic or hydrophobic polymers, copolymers thereof, and mixtures thereof.

Non-limiting example of siloxy-containing polymers that can be used as optical materials are described in U.S. Pat. Nos. 6,762,271; 6,770,728; 6,777,522; 6,849,671; 6,858, 218; 6,881,809; 6,908,978; 6,951,914; 7,005,494; 7,022, 749; 7,033,391; and 7,037,954.

Non-limiting examples of hydrophilic polymers include polymers comprising units of N-vinylpyrrolidone, 2-hydroxyethyl methacrylate, N,N-dimethylacrylamide, methacrylic acid, poly(ethylene glycol monomethacrylate), 1,4-butanediol monovinyl ether, 2-aminoethyl vinyl ether, di(ethylene glycol) monovinyl ether, ethylene glycol butyl vinyl ether, ethylene glycol monovinyl ether, glycidyl vinyl ether, glyceryl vinyl ether, vinyl carbonate, and vinyl carbamate.

Non-limiting examples of hydrophobic polymers include polymers comprising units of $C_1$-$C_{10}$ alkyl methacrylates (e.g., methyl methacrylate, ethyl methacrylate, propyl methacrylate, butyl methacrylate, octyl methacrylate, or 2-ethylhexyl methacrylate; preferably, methyl methacrylate to control mechanical properties), $C_1$-$C_{10}$ alkyl acrylates (e.g., methyl acrylate, ethyl acrylate, propyl acrylate, or hexyl acrylate; preferably, butyl acrylate to control mechanical properties), $C_6$-$C_{40}$ arylalkyl acrylates (e.g., 2-phenylethyl acrylate, benzyl acrylate, 3-phenylpropyl acrylate, 4-phenylbutyl acrylate, 5-phenylpentyl acrylate, 8-phenyloctyl acrylate, or 2-phenylethoxy acrylate; preferably, 2-phenylethyl acrylate to increase refractive index), and $C_6$-$C_{40}$ arylalkyl methacrylates (e.g., 2-phenylethyl methacrylate, 3-phenylpropyl methacrylate, 4-phenylbutyl methacrylate, 5-phenylpentyl methacrylate, 8-phenyloctyl methacrylate, 2-phenoxyethyl methacrylate, 3,3-diphenylpropyl methacrylate, 2-(1-naphthylethyl) methacrylate, benzyl methacrylate, or 2-(2-naphthylethyl) methacrylate; preferably, 2-phenylethyl methacrylate to increase refractive index).

The method of the invention is particularly suited for modifying the refractive index in select regions of an optical, polymeric silicone hydrogel, or an optical, non-silicone hydrogel. For example, we have irradiated a silicone hydrogel that can absorb about 36% by weight water (based on the total hydrated weight). The term "hydrogel" refers to an optical, polymeric material that can absorb greater than 20% by weight water based on the total hydrated weight.

We have irradiated silicon hydrogel optical materials commercially under the trade name Balafilcon™. This silicone hydrogel system is based on a vinyl carbamate substituted TRIS derivative, that is, tris(trimethylsiloxy)silylpropyl vinylcarbamate) (TPVC). The TPVC molecule contains the hydrophobic silicone portion and a vinyl carbamate group. The direct hydrophilic attachment of the carbamate provides the silicone monomer with sufficient hydrophilic character. Also, the vinyl carbamate group provides a polymerizable vinyl group for the attachment of hydrophilic monomers. The resulting silicon hydrogels are transparent, exhibit high Dk and low modulus materials that are insoluble in water.

We have also irradiated a hydrogel copolymer that comprises about 90% (by weight) N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. We have also irradiated HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water. Other optical, polymeric materials that can have its refractive index modified by irradiating select regions with a laser are provided as follows.

In one embodiment, the optical polymeric material can be prepared as a copolymer from at least three monomeric components. The first monomeric component is present in the copolymer in an amount of at least 70% by weight, and its homopolymer will have a refractive index of at least 1.50, preferably at least 1.52 or at least 1.54. The second monomeric component is present in the copolymer in an amount from 3% to 20% or from 3% to 10%, by weight, and its homopolymer will have a glass transition temperature of less than about 300° C., preferably less than about 220° C. The first and second monomeric components together represent at least 80% by weight of the copolymer.

The term "homopolymer" refers to a polymer that is derived substantially completely from the respective monomeric component. Minor amounts of catalysts, initiators and the like can be included, as is conventionally the case, in order to facilitate the formation of the homopolymer. In addition, the homopolymers of both the first and the second monomeric components have sufficiently high molecular weights or degrees of polymerization so as to be useful as IOL materials.

Particularly useful first monomeric components include styrene, vinyl carbazole, vinyl naphthalene, benzyl acrylate, phenyl acrylate, naphthyl acrylate, pentabromophenyl acrylate, 2-phenoxyethyl acrylate, 2-phenoxyethyl methacrylate, 2,3-dibromopropyl acrylate and mixtures thereof. Particularly useful second monomeric components include n-butyl acrylate, n-hexyl acrylate, 2-ethylhexyl acrylate, 2-ethoxyethyl acrylate, 2,3-dibromopropyl acrylate, n-1 1-dihydroperfluorobutyl acrylate and mixtures thereof.

The third monomeric component is best described as a cross-linking monomeric constituent that can form cross-links with the first or the second monomeric components. Preferably, the cross-linking monomeric component is multi-functional and can chemically react with both the first and second monomeric components.

The third component is present in an amount effective to facilitate returning a deformed IOL made by polymerizing the three monomeric components to its original shape in the human eye. The third or crosslinking monomeric component is often present in a minor amount relative to the amounts of the first and second monomeric components. Preferably, the third component is present in the copolymer in an amount of less than about 1% by weight of the copolymer. Examples of useful crosslinking monomeric components include ethylene glycol dimethacrylate, propylene glycol dimethacrylate, ethylene glycol diacrylate and the like and mixtures thereof.

The copolymer can further include a fourth component derived from a hydrophilic monomeric component. This fourth component is present in an amount, from 2% to 20% by weight of the copolymer. The fourth component is preferably present in an amount of less than about 15% by weight of the copolymer. Copolymers which include about 15% by weight or more of a constituent derived from hydrophilic monomeric components tend to form hydrogels if exposed to water.

The term "hydrophilic monomeric component" refers to compounds which produce hydrogel-forming homopolymers, that is homopolymers which become associated with at least 20% of water, based on the weight of the homopolymer, if placed in contact with an aqueous solution. Specific examples of useful hydrophilic monomeric components include N-vinyl pyrrolidone; hydroxyalkyl acrylates and hydroxyalkyl methacrylates, such as 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 2,3-dihydroxypropyl acrylate, 2,3-dihydroxypropyl methacrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and mixtures thereof.

The optical, polymeric materials can also be prepared from monomers having the formula:

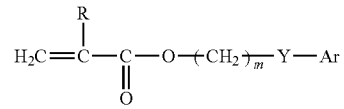

wherein: R is H or $CH_3$; m is 0-10;
Y is nothing, O, S, or NR wherein R is H, $CH_3$, $C_nH_{2n+1}$ (n=1-10), iso $OC_3H_7$, phenyl or benzyl;
Ar is any aromatic ring, such as benzene, which can be unsubstituted or substituted with H, $CH_3$, $C_nH_5$, n-$C_3H_7$, iso-$C_3H_7$, $OCH_3$, $C_6H_{11}$, Cl, Br, phenyl or benzyl; and
a cross-linking monomer having a plurality of polymerizable ethylenically unsaturated groups. The optical material will have a glass transition temperature not greater than 37° C. and an elongation of at least 150%.

Exemplary monomers include, but are not limited to: 2-ethylphenoxy methacrylate, 2-ethylphenoxy acrylate, 2-ethylthiophenyl methacrylate, 2-ethylthiophenyl acrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates.

The copolymerizable cross-linking agent can be any terminally ethylenically unsaturated compound having more than one unsaturated group. Suitable cross-linking agents include, for example: ethylene glycol dimethacrylate, diethylene glycol dimethacrylate, allyl methacrylate, 1.3-propanedioldimethacrylate, allylmethacrylate 1,6-hexanediol dimethacrylate, 1,4-butanediol dimethacrylate, and the like. A preferred cross-linking agent is 1,4-butanediol diacrylate.

The aryl acrylate/methacrylate based optical materials will generally comprise a greater mole percent of acrylate ester residues than of methacrylate ester residues. It is preferred that the aryl acrylate monomers constitute from about 60 mole percent to about 95 mole percent of the polymer, while the aryl methacrylate monomers constitute from about 5 mole percent to about 40 mole percent of the polymer. Most preferred is a polymer comprising about 60-70 mole percent 2-phenylethyl acrylate and about 30-40 mole percent 2-phenylethyl methacrylate.

The optical, polymeric materials can also be prepared from a reinforced cross-linked silicone elastomer which includes a polymer containing 12 to 18 mol percent of aryl substituted siloxane units of the formula $R^4R^5$—SiO. In the formula, $R^4$ and $R^5$ are the same or different and represent phenyl, mono-lower alkyl substituted phenyl groups, or di-lower alkyl substituted phenyl groups. Preferably both $R^4$ and $R^5$ are phenyl.

The polymer has end blockers containing siloxane units of the formula $R^1R^2R^3$—$SiO_5$ wherein $R^1$ and $R^2$ are alkyl, aryl or substituted alkyl or substituted aryl groups, and $R^1$ and $R^2$ can be the same or different. The $R^3$ group of the end blocking siloxane units is an alkenyl group. Preferably, the end blocker is a dimethylvinyl siloxane unit.

The balance of the polymer consists of dialkyl siloxane units of the formula $R^6R^7$—SiO wherein $R^6$ and $R^7$ are the same or different from and are methyl or ethyl groups, and the polymer has a degree of polymerization from 100 to 2000. Preferably, $R^6$ and $R^7$ are both methyl, and the degree of polymerization is approximately 250.

A trimethyl silyl treated silica reinforcer is finely dispersed in the polymer, in a weight ratio of approximately 15 to 45 parts of the reinforcer to 100 parts of the polymer. Preferably, there is approximately 27 parts of reinforcer to 100 parts of the copolymer.

The optical, polymeric material can also be prepared by polymerizing the following monomeric components: (A) 5-25% by weight of acrylate represented by the general formula

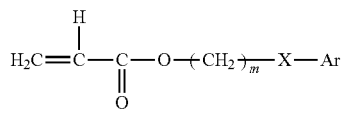

wherein Ar represents an aromatic ring of which hydrogen atom may be substituted by a substitutional group, X represents an oxygen atom or a direct bonding, and m represents an integer of 1 to 5; (B) 50 to 90% by weight of 2-hydroxyethyl(meth)acrylate; and (C) 5 to 45% by weight of a (meth)acrylate monomer though not of the formula that represent monomer (A) and not 2-hydroxyethyl(meth)acrylate. Also, the coefficient of water absorption of the homopolymer of monomer (C) is not more than 30% by weight.

In the present invention the coefficient of water absorption is defined as the following equation: water absorption (% wt)=$(W-W_o)/W_o \times 100$ wherein the value is calculated at 25° C. by using the specimen having 1 mm thickness at cutting, W represents a weight of the specimen in equilibrium state of water, and $W_o$ represeents a weight of the specimen in a dry state.

An exemplary listing of(meth)acrylate monomer (C) include an alkyl(meth)acrylate containing a straight chain, a branched chain or cyclic chain such as methyl(meth)acrylate, ethyl(meth)acrylate, propyl(meth)acrylate, butyl(meth) acrylate, pentyl(meth)acrylate, hexyl meth)acrylate, heptyl (meth)acrylate, nonyl(meth)acrylate, stearyl meth)acrylate, octyl(meth)acrylate, decyl(meth)acrylate, lauryl(meth)acrylate, pentadecyl(meth)acrylate, 2-ethylhexyl(meth)acrylate, cyclopentyl(meth)acrylate, (meth)acrylate, cyclohexyl (meth)acrylate: an alkyl(meth)acrylate containing 1 to 5 carbon atoms of alkyl group: a hydroxyalkyl(meth)acrylate containing a straight chain, a branched chain or cyclic chain, except for 2-HE(M)A (B), and any mixture thereof. Among the alkyl methacrylates those containing 1 to 3 carbon atoms of alkyl group are preferred. Among the hydroxyalkyl methacrylates those containing 3 to 6 carbon atoms of hydroxyalkyl group are preferred.

The optical, polymeric material can also be prepared by copolymerizing a specific monomer mixture comprising perfluorooctylethyloxypropylene(meth)acrylate, 2-phenylethyl(meth)acrylate, an alkyl(meth)acrylate monomer having the following general formula,

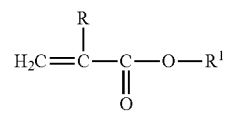

wherein R is hydrogen or methyl and $R^1$ is a linear or branched $C_4$-$C_{12}$ alkyl group, and a crosslinking monomer. An exemplary list of alkyl(meth)acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene(meth)acrylate is present from 5% to 20% by weight, the 2-phenylethyl(meth) acrylate is present from 40% to 60% by weight, the alkyl (meth)acrylate monomer is present from 30% to 50% by weight and the crosslinking agent is present from 0.5% to 4% by weight.

The optical, polymeric material can also be prepared from a first (meth)acrylate monomer, a second aromatic monomer, and a third, high water content hydrogel-forming monomer. The first monomeric component is present from 30% to 50% by weight, the second monomeric component is present from 10% to 30% by weight, and the third monomeric component is present from 20% to 40% by weight. A crosslinking agent is also used to prepare the material.

The first monomeric component is an aryl acrylate or an aryl methacrylate, and are commonly referred to as aryl (meth)acrylate monomers. The term "aryl" implies that the compound contains at least one aromatic group. Exemplary aryl(meth)acrylate monomers include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenylethyl methacrylate, 2-(4-propylphenyl)ethyl methacrylate, 2-(4-(1-methylethyl)pheny)ethyl methacrylate, 2-(4-methoxyphenyl)ethylmethacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

The second monomeric component includes a monomer having an aromatic ring with a substituent having at least one site of ethylenic unsaturation. Preferably, this second monomeric component is not an acrylate. Such monomers have the general formula:

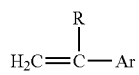

wherein X is H or $CH_3$, and Ar is a substituted or unsubstituted aromatic ring. Representative second monomeric components include, for example, substituted and unsubstituted styrene compounds. These compounds may be substituted with hydrogen, halogen (e.g. Br, Cl, F), lower alkyl groups (e.g. methyl, ethyl, propyl, butyl, isopropyl), and/or lower alkoxy groups. Suitable aromatic monomers include, for example: styrene, methoxy styrene, and chlorostyrene.

The third monomeric component comprises a high water content hydrogel-forming monomer. Preferably, the third monomeric component includes a methacrylate without an aromatic substituent. Suitable high water content hydrogel-forming monomers include, for example: hydroxyethyl methacrylate (HEMA), hydroxyethoxyethyl methacrylate (HEEMA), hydroxydiethoxyethyl methacrylate, methoxyethyl methacrylate, methoxyethoxyethyl methacrylate, methoxydiethoxyethyl methacrylate, ethylene glycol dimethacrylate, n-vinyl-2-pyrrolidone, methacrylic acid, vinyl acetate and the like and mixtures thereof. One skilled in this art will recognize that many other high water content hydrogel-forming monomers are likely to be operable in view of this disclosure. HEMA and HEEMA are two of the more preferred third monomeric components.

The copolymer may also include a crosslinking agent. The copolymerizable crosslinking agent(s) useful in forming the copolymeric material of the invention include any terminally ethylenically unsaturated compound having more than one unsaturated group. Preferably, the crosslinking agent includes a diacrylate or a dimethacrylate. The crosslinking agent may also include compounds having at least two (meth)acrylate and/or vinyl groups. Particularly preferred crosslinking agents include diacrylate compounds The optical, polymeric materials are prepared by generally conventional polymerization methods from the respective monomeric components. A polymerization mixture of the monomers in the selected amounts is prespared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butulcyclohexyl) peroxydicarbonate, azonitriles, such as azobisisobytyronitrile, and the like. A preferred initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

EXAMPLES

Example 1

Forming Structures in Optical Polymeric Materials

The optical system described was used to form line structures in select regions of optical materials. Experiments were conducted with three polymeric materials (Bausch & Lomb Incorporated, Rochester, N.Y.): PV2526-164, RD1817, and HEMA B. PV2526-164 is a silicone-containing hydrogel that can absorb about 36% (by total weight). RD 1817 is a hydrogel copolymer that comprises about 90% (by weight) N-vinylpyrrolidone ("NVP") and about 10% (by weight) 4-t-butyl-2-hydroxycyclohexyl methacrylate and that can absorb about 80% (by weight) water. Its refractive index when hydrated is very close to the index of water. HEMA B is poly(2-hydroxyethyl methacrylate) cross-linked with about 0.9% (by weight) of ethylene glycol dimethacrylate ("EGDMA"), also a hydrogel, which can absorb about 37% (by weight) water. The refractive indices of PV2526-164, RD1817, and HEMA B are 1.422, 1.363, and 1.438, respectively, when they are in the hydrated state. Each of the hydrogel samples was maintained in a solution (Bausch and Lomb "Renu" solution) between a microscope slide and a glass cover slip to maintain their water-content during micro-machining and subsequent optical measurements. The thickness of these hydrogel samples in the solution is about 700 μm. The hydrated sample was mounted horizontally on the scanning platform, and the femtosecond laser beam was directed vertically downward through the high-numerical-aperture objective and was focused inside the bulk material, as shown in Figure B, at a depth of about 100 μm from the upper surface of the sample. Periodic gratings structures were created with a scanning speed of 0.4 μm/sec in an X-Y plane perpendicular to the laser beam. An Olympus BX51 Model microscope was used to observe the gratings that were created inside these three materials.

The microscope images showed periodically parallel gratings inside the samples with 5-μm spacing. The gratings were difficult to see in bright-field microscope, indicating that these gratings exhibit low scattering. The width of the gratings was about 1 μm, which was significantly smaller than the laser focus diameter of 2.5 μm that was measured using a knife-edge method. Therefore, the modified region is still within the laser irradiation focus volume although there would be heat accumulation generated in the process.

A cross section of the PV2526-164 sample revealed that the cross section of the gratings was elliptical with the longer axis oriented in the direction of the laser beam, indicating that there was a larger laser intensity distribution in this direction. By carefully adjusting the cover-slip correction of the objective, this spherical aberration could be minimized.

These gratings were investigated by focusing an unpolarized He—Ne laser beam with a wavelength of 632.8 nm on these gratings and monitoring the diffraction pattern. The diffraction angles showed good agreement with the diffraction equation $$m\lambda = d \sin \theta \quad (1)$$

where m is the diffraction order, $\lambda$ is the wavelength of the incident laser beam which here is 632.8 nm, and d is the grating period.

The diffraction efficiency of the grating can be measured, and since the efficiency is a function of the refractive index change, it may be used to calculate the refractive index change in the laser irradiation region. Consider the grating as a phase grating, its transmittance function could be written as $$t(x_0, y_0) = (e^{i\phi_2} - e^{i\phi_1}) \text{rect}\left(\frac{x_0}{a}\right) * \frac{1}{d} \text{comb}\left(\frac{x_0}{d}\right) + e^{i\phi_1} \quad (2)$$

where a is the grating line width, d is the groove spacing, $\phi_2$ and $\phi_1$ are the phase delays through the lines and ambient region respectively, $$\phi_2 = 2\pi \times \frac{(n + \Delta n) \times b}{\lambda} \text{ and } \phi_1 = 2\pi \times \frac{n \times b}{\lambda},$$

b is the thickness of the grating line, n is the average refractive index of the material, $\Delta n$ is the average refractive index change in the grating lines, and $\lambda$ is the incident light wavelength of the measurement (632.8 nm). Here, the grating line width is 1 μm and the thickness is 3 μm. The index change within the laser effect region can be approximated to be uniform. The convolution theorem can be used to calculate the spectrum of the grating such as $$T(f_x, f_y) = F\{t(x_0, y_0)\} = (e^{i\phi_2} - e^{i\phi_1}) a \sin c(af_x) \text{comb}(df_x) \delta(f_y) + e^{i\phi_1} \delta(f_x, f_y) \quad (3)$$

Then, the intensity distribution of the grating diffraction pattern is:

$$I(x, y) = \left(\frac{1}{\lambda z}\right)^2 \times \quad (4)$$

$$\left[(e^{i\phi_2} - e^{i\phi_1}) \frac{a}{d} \sum_{n=-\infty}^{\infty} \text{sinc}\left(\frac{an}{d}\right) \delta\left(\frac{x}{\lambda z} - \frac{n}{d}, \frac{y}{\lambda z}\right) + e^{i\phi_1} \delta\left(\frac{x}{\lambda z}, \frac{y}{\lambda z}\right)\right]^2$$

From this formula, the intensity of the $0^{th}$ ($I_0$), $1^{st}$ ($I_1$), and $2^{nd}$ ($I_2$) order diffraction light is $$I_0 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right) \frac{a}{d} + e^{i2\pi \times \frac{n \times b}{\lambda}}\right]^2 \quad (5)$$

$$I_1 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right) \frac{a}{d} \text{sinc}\left(\frac{a}{d}\right)\right]^2 \text{ and} \quad (6)$$

$$I_2 = \left(\frac{1}{\lambda z}\right)^2 \times \left[\left(e^{i2\pi \times \frac{(n+\Delta n) \times b}{\lambda}} - e^{i2\pi \times \frac{n \times b}{\lambda}}\right) \frac{a}{d} \text{sinc}\left(\frac{2a}{d}\right)\right]^2 \quad (7)$$

By comparing the light intensities of $1^{st}$, $2^{nd}$ and $0^{th}$ diffraction orders, the refractive index change within the grating lines can be determined. FIG. 3 shows the ratio of intensity of the $1^{st}$ and $2^{nd}$ diffraction order to $0^{th}$ order of the grating in PV2526-164 is 0.1374 and 0.0842 respectively, and the corresponding refractive index change determined by the analysis is about 0.06. Using the same method, we determined the average refractive index change in RD1817 and HEMA B to be 0.05±0.0005 and 0.03±0.0005. Thus, it was demonstrated that the refractive index of a material can be modified by applying an ultrafast laser thereto.

Figure 9A:
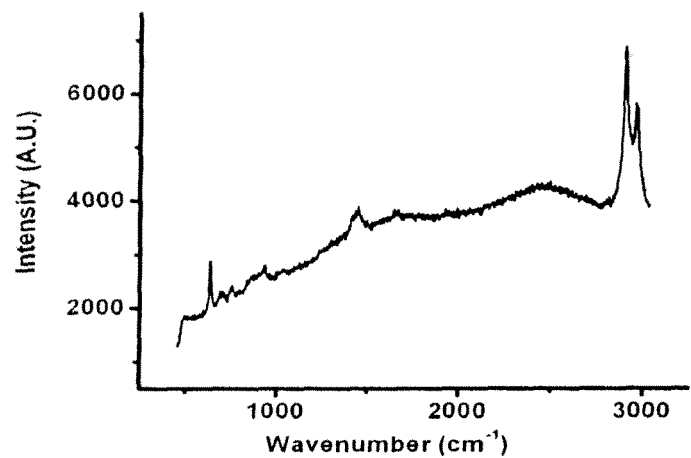
FIGS. 9A and 9B show the Raman spectra of the base material and the irradiated regions of balafilconA.
Figure 9B:
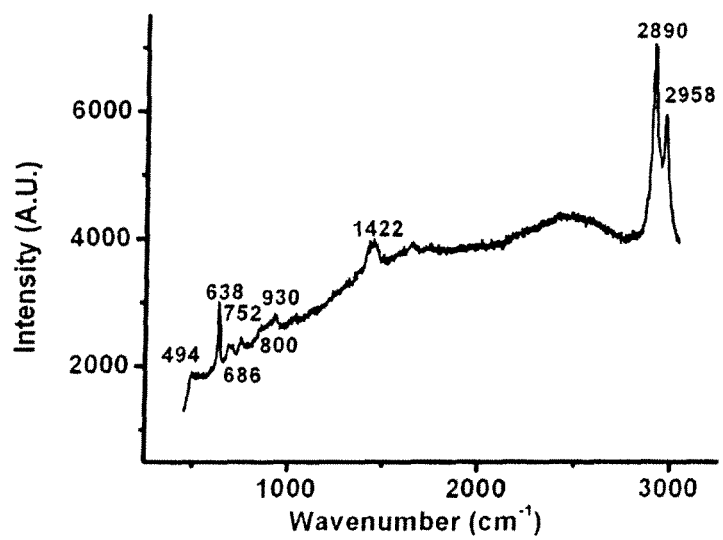

We used Raman spectroscopy to provide information on the structural or molecular changes that occur in the irradiated regions on the optical, polymeric materials. In the Raman scattering experiments, the hydrogel polymer samples are placed in a confocal micro-Raman spectrometer equipped with an X-Y scan stage with nanometer resolution. A 632.8 nm He—Ne laser is focused on the surface of the material in order to obtain the Raman scattering signal. Due to the difference between the refractive indices of the bulk and the irradiated regions, the scattered light at the interface was monitored in order to ensure the laser focus was located into the irradiated region. FIGS. 9A and 9B show the Raman spectra of the base material and the irradiated region (micromachined feature) of the hydrogel, respectively. The main Raman peaks are centered at 2890 cm$^{-1}$ and 2958 cm$^{-1}$ (—CH$_x$ bond stretching), 1422 cm$^{-1}$ (—CH$_x$ bond deformation), 930 cm$^{-1}$ (C—C bond skeletal), 800 cm$^{-1}$ (—Si—O—Si— bond stretching), 686 cm$^{-1}$ to 752 cm$^{-1}$ (—Si—(CH$_3$)$_x$ bond stretching) and 638 cm$^{-1}$ (—Si—O$_3$ bond stretching) [4]. Comparing the two spectra strongly suggests there is no significant structural or chemical change between the irradiated regions and the base material.

The above Raman results are surprising in light of recent Raman spectra analysis of fused silica modified by femtosecond laser pulses. See, J. W. Chan, T. Huser, S. Risbud, D. M. Krol, in "*Structural changes in fused silica after exposure to focused femtosecond laser pulses,*" Opt. Lett. 26, 1726-1728 (2001)). The results of our Raman experiments, however, may explain why we do not observe any light scattering by the irradiated regions (micromachined structures) in the optical materials. Our Raman spectra also suggest that low-pulse-energy femtosecond irradiation of optical, polymeric materials do not cause strong structural changes in the materials, even when the change of the refractive index is much higher than that obtained for fused silica.

Figure 10:
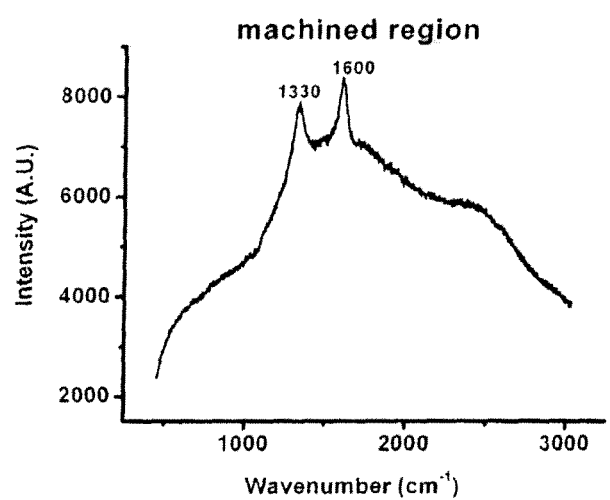
FIG. 10 shows the Raman spectrum of a region of balafilcon A irradiated with relatively high energy, femtosecond laser pulses.

FIG. 10 shows the Raman spectrum of a damage spot in balafilconA, if higher energy femtosecon pulses are used in the irradiation (micromachining) process. Only Raman bands related to disordered carbon are detected (D band at ~1330 cm$^{-1}$ and G band at ~1600 cm$^{-1}$) indicating that the chemical bonds forming the hydrogel structure are broken.

Figure 11:
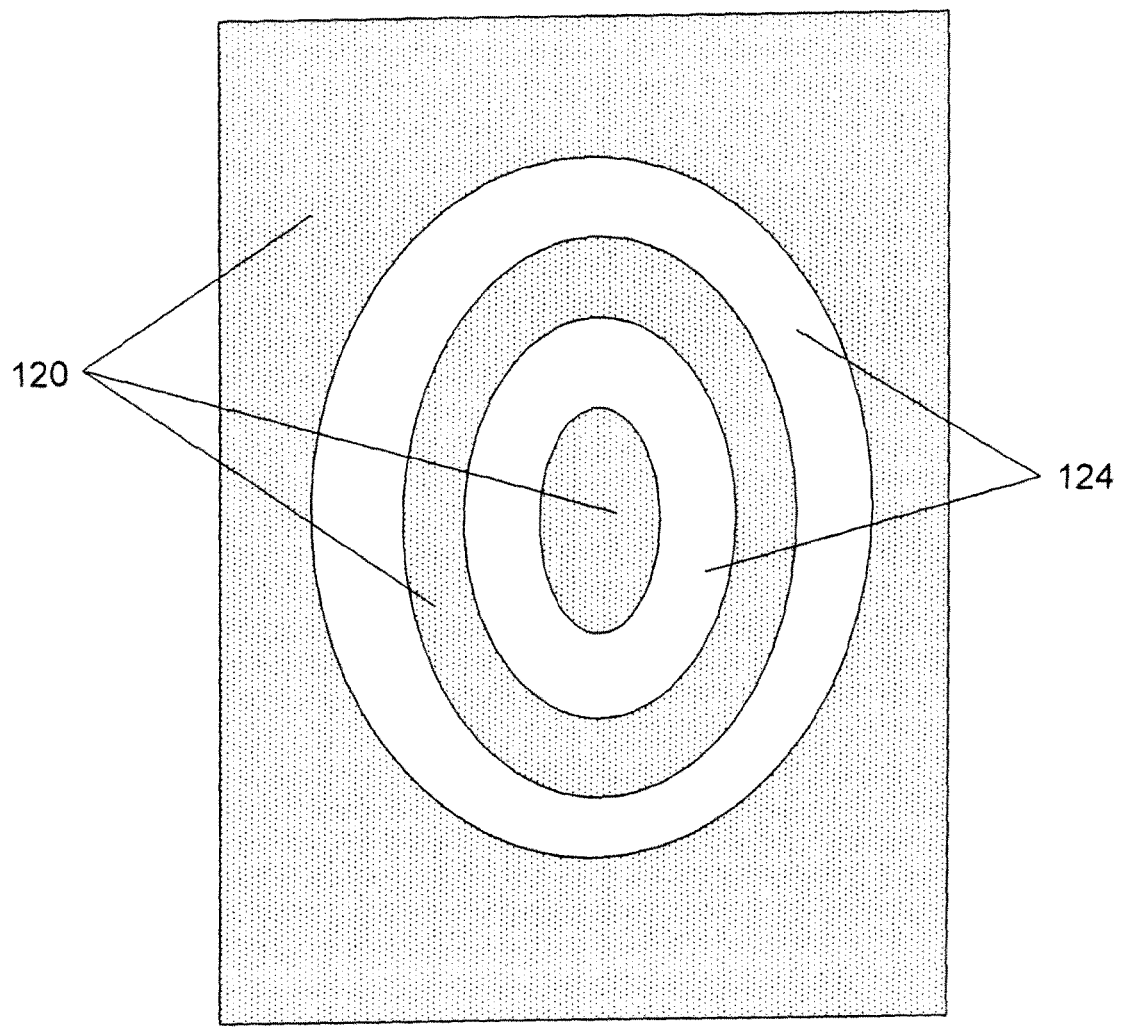
FIG. 11 shows a radial (micromachined) refractive structure in an acrylic IOL material.

We also irradiated an acrylic material comprising about 80 wt % HEMA and 20 wt % MMA with a water content of about 26% using similar process conditions described above. Such a material is representative of Bausch & Lombs intraocular lens sold under the tradename Akreos®. FIG. 11 shows a radial pattern micromachined into the acrylic material. FIG. 11 is a pictorial representation of the optical material with non-irradiated regions 120 and irradiated (micromachined) regions 124.

We also irradiated a silicone hydrogel material using similar process conditions described above. Such a material is representative of Bausch & Lombs intraocular lens marketed under the tradename SoFlex®SE. A similar radial pattern as shown in FIG. 11 was micromachined into the silicone material.

Although the foregoing Examples describes a creation of grating lines, cylinders and radial patterns in optical materials, other features also can be created using a method of the present invention. For examples, arrays of dots (e.g., having a dimension in the nanometer range) can be created by directing the laser beam at discrete points or spots within the material. Such an array can be arranged substantially on one plane or several such arrays can be created at different depths within the material. A material thus modified can be advantageously useful when light is not substantially scattered by the dots.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

We claim:

1. A method of changing the index of refraction of an optical hydrogel that is a component of an optical device for vision correction, the method comprising: providing a physician with a laser system to irradiate select regions of the optical hydrogel following implantation of the optical device into the eye of the patient, the laser system comprising a laser having a laser pulse energy from 0.01 nJ to 50 nJ and a light wavelength from 600 nm to 900 nm; wherein the irradiated regions are formed by scanning the laser light in an X-Y plane, the irradiated regions characterized by a positive change in refractive index of from 0.01 to 0.06.

2. The method of claim 1 wherein the irradiated regions comprise an area or volume filled structure.

3. The method of claim 2 wherein the area or volume filled structure is defined by a series of line scans, the line scans having a width from 0.2 µm to 3 µm, and a height from 0.4 µm to 8 µm, wherein the height is measured in a Z-direction parallel to the laser beam.

4. The method of claim 3 wherein the laser light has a pulse width and the laser system includes negative compensation to compensate for a positive dispersion of the laser pulse width introduced by focusing objectives.

5. The method of claim 2 wherein the area or volume filled structure is a vertically stacked structure wherein the irradiated regions are formed separately in different planes in the hydrogel in a Z-direction parallel to the laser beam.

6. The method of claim 2 wherein the laser light has a pulse energy from 0.2 nJ to 10 nJ.

7. The method of claim 1 wherein the optical device is selected from an intraocular lens, a corneal inlay, a corneal ring or a keratoprothesis.

8. A method for modifying the refractive index of an optical, polymeric material, the method comprising irradiating select regions of the optical, polymeric material with a focused, visible or near-IR laser having a pulse energy from 0.05 nJ to 1000 nJ, wherein the irradiated regions exhibit a change in refractive index of at least 0.01.

9. The method of claim 8 wherein the irradiated regions and regions having no irradiation have no significant differences in the Raman spectrum.

10. The method of claim 8 wherein the pulse energy of the laser is from 0.2 nJ to 100 nJ.

11. The method of claim 10 wherein the visible or near-IR laser generates pulses having a pulse width of 4 fs to 100 fs.

12. The method of claim 11 wherein the the pulse width is maintained by a compensation scheme selected from the group consisting of at least two prisms and at least one mirror, at least two diffraction gratings, a chirped mirror and dispersion compensating mirrors to compensate for positive dispersion introduced by a focus objective.

13. The method of claim 8 wherein the pulse energy of the laser is from 0.5 nJ to to 10 nJ.

14. The method of claim 8 wherein the region of the optical material irradiated by the laser exhibits a positive change in the refractive index from 0.02 to 0.06.

15. The method of claim 8 wherein the optical material is an intraocular lens that has been positioned in the lens capsule of a patient.

16. The method of claim 8 wherein the optical, polymeric material is a hydrogel.

17. The method of claim 8 wherein the optical polymeric material is formed into an optical device containing the irradiated regions.

18. The method of claim 17 wherein the step of irradiating select regions forms a three dimensional structure within the optical device.

19. The method of claim 17 in which the optical device is selected from the group consisting of an intraocular lens, a corneal inlay, a corneal ring or a keraprothesis.

20. The method of claim 19 wherein the optical polymeric material is prepared from (meth)acrylate monomer selected from the group consisting of 2-hydroxymethyl (meth)acrylate, 2-phenylethyl (meth)acrylate, methyl(meth)acrylate and 3-phenylpropyl (meth)acrylate.

* * * * *